United States Patent [19]

Jacobi et al.

[11] 4,271,389
[45] Jun. 2, 1981

[54] METHOD AND APPARATUS FOR PHYSIOLOGIC FACSIMILE IMAGING OF BIOLOGIC TARGETS WITHOUT MULTIPATH CONTAMINATION USING REMOTE MICROWAVE INTERROGATION

[75] Inventors: John H. Jacobi, Bowie; Lawrence E. Larsen, Silver Spring, both of Md.

[73] Assignee: The United States of America as represented by the Secretary of the Army, Washington, D.C.

[21] Appl. No.: 45,442

[22] Filed: Jun. 4, 1979

Related U.S. Application Data

[63] Continuation-in-part of Ser. No. 41,374, May 22, 1979, which is a continuation-in-part of Ser. No. 891,256, Oct. 14, 1977, which is a continuation-in-part of Ser. No. 842,137, Oct. 14, 1977, Pat. No. 4,135,131.

[51] Int. Cl.³ ............................................. G01R 27/04
[52] U.S. Cl. .................................. 324/58.5 A; 73/602
[58] Field of Search .......... 324/58, 5 A, 58 A, 57 SS; 73/602, 619, 620; 128/653, 660

[56] References Cited

U.S. PATENT DOCUMENTS

| | | | |
|---|---|---|---|
| 4,121,468 | 10/1978 | Glover et al. ........................... | 73/602 |
| 4,176,658 | 12/1979 | Kossoff et al. ..................... | 73/602 X |

*Primary Examiner*—Stanley T. Krawczewicz
*Attorney, Agent, or Firm*—William G. Gapcynski; Werten F. W. Bellamy; Sherman D. Winters

[57] ABSTRACT

A physiologic facsimile image of a biological target without multipath contamination is obtained by first producing, for each one of a plurality of sample locations which are spaced so as to define a two-dimensional array, a time delay spectrum wherein the frequency of each spectral ordinate represents the instantaneous differential propagation delay between a first microwave signal which has been propagated through the target and a second microwave signal which initially corresponds to the first microwave signal, and which has been propagated through means having a predetermined propagation delay, and measuring the amplitude of the spectral ordinate corresponding to the direct ray path of propagation through the target, so as to obtain a set of data. The set of data is then digitized and converted from time domain to frequency domain. The transformed data is then processed by sorting the data into column order; magnifying data derived from the sorting step so as to enhance and preserve the resolution of the image; mapping data derived from the magnifying step into further data using a predetermined mapping function so as to enhance the contrast between selected portions of the image; and obtaining a set of control signals which are used to actuate a display device to generate the facsimile image by filtering data derived from the mapping step using a band pass function which rejects spatial frequencies below a predetermined first frequency and/or rejects spatial frequencies above a predetermined second frequency so as to minimize, respectively, the effects of variations in the thickness of the target and/or spurious frequencies resulting from the magnifying step.

19 Claims, 8 Drawing Figures

METHOD AND APPARATUS FOR PHYSIOLOGIC FACSIMILE IMAGING OF BIOLOGIC TARGETS WITHOUT MULTIPATH CONTAMINATION USING REMOTE MICROWAVE INTERROGATION

CROSS-REFERENCE TO RELATED APPLICATION

The present application is a continuation-in-part of a copending application entitled "Method and Apparatus for Physiologic Facsimile Imaging of Biologic Targets Based on Complex Permittivity Measurements Using Remote Microwave Interrogation", hereinafter referred to as "Physiologic Facsimile Imaging", Ser. No. 41,374, filed on May 22, 1979, which in turn is a continuation-in-part of a copending application, Ser. No. 891,256, entitled "Ridged Waveguide Antenna Submerged in Dielectric Liquid", filed on Oct. 14, 1977, which in turn is a continuation-in-part of an application, Ser. No. 842,137, filed on Oct. 14, 1977, now issued as U.S. Pat. No. 4,135,131.

FIELD OF THE INVENTION

The present invention relates in general to methods and apparatus for producing facsimile images of scanned targets, and in particular, to methods and apparatus for remote microwave interrogation and physiologic imaging of biological targets.

BACKGROUND OF THE INVENTION

As discussed in detail in applicants' aforementioned copending applications, each of which hereby is expressly incorporated herein by reference, microwave radiation is uniquely advantageous for the investigation of biological targets since facsimile images indicative of the physiologic and pathophysiologic states thereof may be produced by the noninvasive microwave interrogation and imaging techniques invented by applicants. However, a major source of image contamination using microwave imaging techniques is multipath propagation. It is thus a principal object of the present invention to minimize such image contamination.

A further object of the present invention is to allow unambiguous determination of the time delay and attenuation of microwave energy propagating through biological targets.

SUMMARY OF THE INVENTION

These and other objects of the present invention are achieved by measuring the attenuation and phase shift of a microwave signal propagated through a biological target using applicants' microwave time delay spectroscopy techniques to derive data for a range of propagation delays corresponding to the direct ray path through the target, and producing an image from data derived for a plurality of such measurements in accordance with the imaging techniques disclosed in applicants' aforementioned copending "Physiologic Facsimile Imaging" application.

More particularly, the present invention entails producing a time delay spectrum for each one of a plurality of sample locations which are spaced so as to define a two-dimensional array, wherein the frequency of each spectral ordinate of the time delay spectrum represents the instantaneous differential propagation delay between a first microwave signal which has been propagated through the target and a second microwave signal, initially corresponding to said first microwave signal, which has been propagated through means having a predetermined propagation delay, and measuring the amplitude of the spectral ordinate corresponding to the direct ray path of propagation through the target, so as to obtain a set of data. The set of data is then processed so as to obtain a corresponding set of control signals for the display device, and the control signals are used to produce a two-dimensional image array on the display device.

The processing step of the present invention advantageously comprises the steps of: digitizing the set of data if it was not in digital form; transforming the data from time domain to frequency domain; sorting the set of data into column order; magnifying data derived from the sorting step so as to enhance and preserve the resolution of the image; mapping data derived from the magnifying step into further data using a predetermined mapping function so as to enhance the contrast between selected portions of the image; and obtaining the set of control signals by filtering data derived from the mapping step using a band pass function which rejects spatial frequencies below a predetermined first frequency and/or rejects spatial frequencies above a predetermined second frequency so as to minimize, respectively, the effects of variations in the thickness of the target and/or spurious frequencies resulting from the magnifying step.

Other features and advantages of the invention will be set forth in, or apparent from, the detailed description of the preferred embodiments found hereinbelow.

DETAILED DESCRIPTION OF THE PREFERRED EMBODIMENTS

Figure 1:
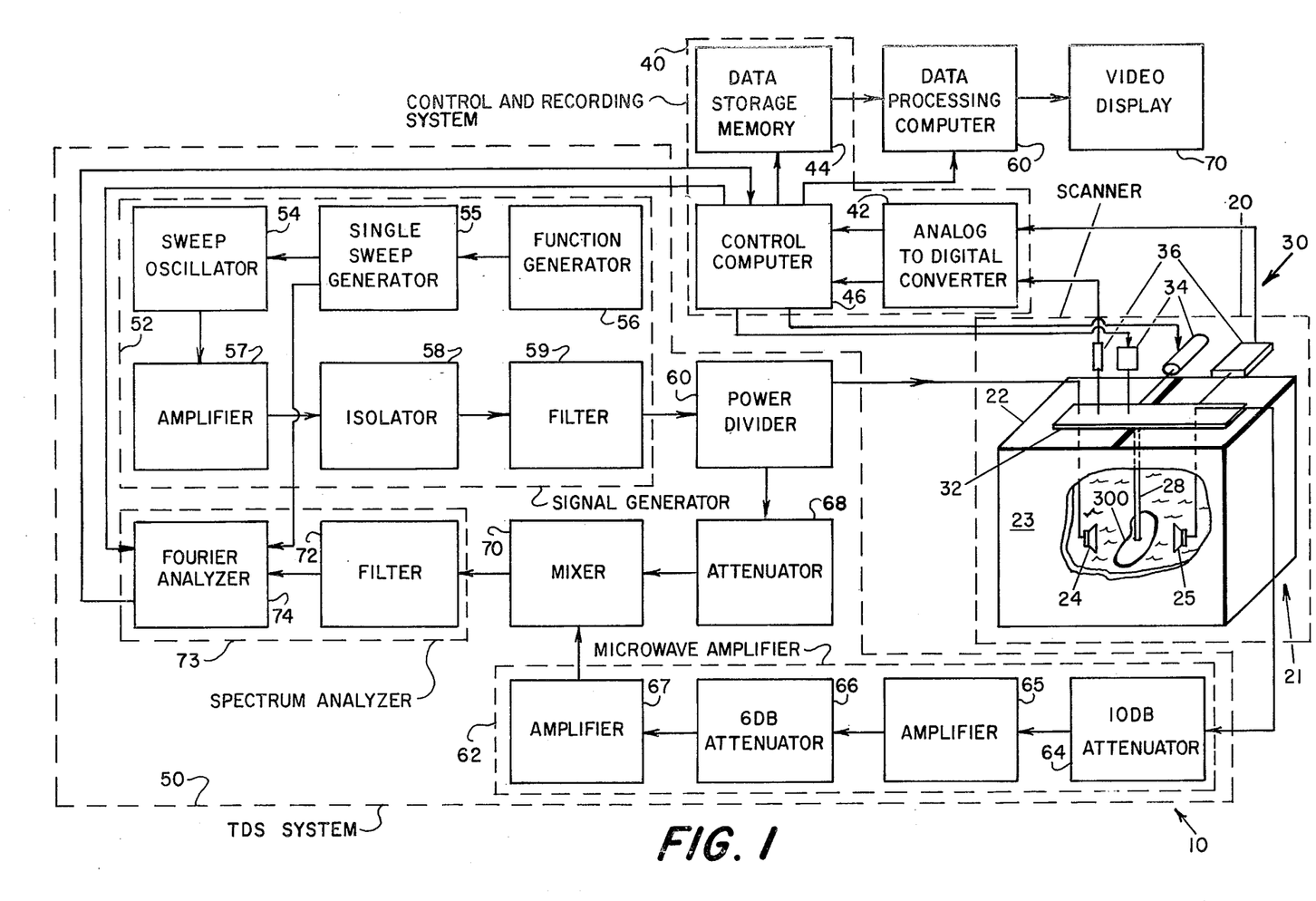
FIG. 1 is a schematic block diagram of apparatus for interrogating and imaging a target in accordance with the present invention.

In accordance with the present invention, the first step in obtaining a facsimile image of a biological target in which multipath contamination is minimized is to transmit a constant amplitude, swept frequency microwave signal through the target at each one of a plurality of sample locations which are spaced so as to define a two-dimensional array, and to analyze the transmitted signal for each sample location using time delay spectroscopy techniques to derive the signal data corresponding to the direct path for the corresponding sample location. A system for performing this transmitting and analyzing step advantageously is constructed in accordance with the teachings of applicant's aforementioned copending "Physiologic Facsimile Imaging" application filed on May 22, 1979. Such a system is illustrated in FIG. 1. The system, which is generally denoted 10, basically comprises an electromechanical scanner, generally denoted 20, a control and recording system, generally denoted 40; and a time delay spectroscopy (TDS) system, generally denoted 50.

As shown in FIG. 1, electromechanical scanner 20 comprises a remote interrogation system, generally denoted 21; positioning apparatus, generally denoted 30; and a target mounting arm 28.

Interrogation system 21 preferably is of the type disclosed in applicant's aforementioned copending "Physiologic Facsimile Imaging" application. Specifically, as shown in FIG. 1, system 21 advantageously comprises a tank 22 containing a body 23 of water, or other high relative dielectric constant (e.g., $K' = 80$) medium, in which a transmitting antenna 24, a receiving antenna 25, and a biological target 300 to be imaged are immersed such that the antenna and target are coupled by means of the dielectric medium.

Tank 22 preferably is dimensioned large enough so as to minimize reflections from the walls of the tank. However, as is noted in applicants' aforementioned copending application Ser. No. 891,256, such reflections are minimized by applicants' lossy dielectric coupling medium interrogation system and thus tank 22 need not be an anechoic chamber. A cubical embodiment of tank 22 which is 0.914 M on a side has been found to be suitable for imaging of canine kidney targets. Preferably, the dielectric medium constituting body 23 is iodinated to kill bacteria, and is continuously filtered using apparatus (not shown), such as ion-exchange columns, to remove solutes.

Antennas 24 and 25 preferably are large bandwidth, small aperture antennas having frequency independent phase centers, such as the type disclosed in applicants' aformentioned copending application, Ser. No. 891,256. The antennas advantageously are configured for optimum performance over a bandwidth corresponding to the frequency range of the interrogation microwave signal.

Positioning apparatus 30 comprises conventional X and Y coordinate (horizontally and vertically displaceable) translating arms, which are schematically depicted and are generally denoted 32; an independently controlled conventional stepping motor 34 connected to each translating arm 32 for displacement thereof; and a conventional position transducer 36 connected to each translating arm 32 for monitoring the position thereof, such that closed loop positional accuracy can be obtained. Apparatus 30 preferably should have a positional accuracy of at least 0.003 mm over a range of approximately 200 mm.

Antennas 24 and 25 are mounted to translating arms 32 so as to be disposed in a predetermined spaced relationship with respect to each other and so as to be displaced by translating arms 32 in spatial synchronism. Spacing of antennas 24 and 25 such that the facing flanges thereof are separated by a distance of approximately 5 cm, and are separated from a target 300 disposed therebetween at its thickest dimension in the direction of propagation by a distance of approximately 2-3 mm, has been found to be advantageous using the preferred apparatus specified herein. The maximum spacing between antennas 24 and 25 for which imaging data may be obtained is a function of the propagation loss properties of the target and the dielectric medium constituting body 23 (and thus the frequency of the interrogating radiation), the sensitivity of TDS system 50, and, ultimately, the noise inherent in the apparatus, including the thermal noise properties of the target and the antennas 24 and 25.

Mounting arm 28 is composed of a material having a high relative complex permittivity $K^*$, such as ceramic filled by titanium dioxide, and is configured such that a target 300 mounted thereon is disposed intermediate antennas 24 and 25. Weights (not shown) may also be provided which are suspended from target 300 in order to counteract the buoyancy thereof when submerged in body 23 of the dielectric medium.

Control and recording system 40 comprises a conventional analog-to-digital converter 42 which converts the outputs of position transducers 36 into digital X-Y coordinate information, a conventional electronic data storage memory 44; and a control computer 46 which advantageously is implemented by programming a conventional general purpose computer in accordance with conventional programming techniques to provide control signals for controlling the operation of scanner 20 and TDS system 50 in the manner to be described in more detail hereinbelow. A Heidenhain "POS-ECON 1" readout advantageously comprises converter 42 (as well as transducers 36) a Hewlett Packard HP 7900A disc memory and/or HP 7970B tape memory advantageously comprises memory 44 and a Hewlett Packard HP 2100A minicomputer and associated Tektronix 4013 terminal advantageously comprises computer 46.

Still referring to FIG. 1, TDS system 50 comprises a swept frequency microwave signal generator, generally denoted 52, for generating an output from which the interrogating microwave signal is produced, a conventional power divider 60 for dividing the output of generator 52 into two equal signals, a first one of which is connected to transmitting antenna 24; a microwave amplifier, generally denoted 62, connected to receiving antenna 25 for amplifying the signal produced thereby so as to overcome the signal to noise ratio difficulties of long path lengths; a conventional mixer 70 for heterodyning the output of amplifier 62 with the output of a conventional attenuator 68 fed by the second one of the signals produced by divider 60 to produce a waveform which, when Fourier transformed, becomes a time delay spectrum; and a spectrum analyzer 73 for analyzing the output of mixer 70 to determine the ordinate or frequency thereof corresponding to direct path propagation of the interrogating microwave signal transmitted through target 300.

Signal generator 52 preferably comprises, as shown, a conventional sweep oscillator 54 controlled by a conventional single sweep generator 55 and associated function generator 56, which vary the output of oscillator 54 linearly by applying a voltage ramp function as a frequency modulation input thereto. Varying the oscillator frequency from approximately 3142 MHz to 3763 MHz with a ramp of 15 msec duration has provded advantageous. A Hewlett Packard HP 8690B oscillator and Wavetek 185 function generator advantageously comprise oscillator 54 and generator 56, respectively.

Generator 55 advantageously is configured, as is schematically shown, to generate a trigger pulse simultaneously with the onset of the sweep function to trigger analyzer 73. A constant current source charging a capacitor (not shown) advantageously comprise generator 55.

Signal generator 52 further preferably comprises a conventional microwave power amplifier 57 for amplifying the output of oscillator 54, a conventional isolator 58 to protect amplifier 57 from excessive reflected power, and a conventional low pass filter 59 to reject harmonics in the signal fed to antenna 24. Amplifier 57 preferably has a low power output, on the order of one watt, to prevent significant heating of the components of interrogation system 21, which would adversely affect the performance thereof. Filter 29 preferably has a cutoff frequency of 4 GHz. A Hewlett Packard HP291C travelling wave tube (TWT) amplifier, E-M Labs S11P isolator, and Microlab LA-4ON filter advantageously comprise amplifier 57, isolator 58, and filter 59, respectively. Amplifier 62 advantageously comprises a conventional 10 dB attenuator 64 connected in series with two low noise amplifiers 65 and 67 which are coupled by a conventional 6 dB attenuator 66, as shown in FIG. 1. Attenuator 68 is preferably configured so as to provide an attenuation factor of 20 dB. Spectrum analyzer 73 advantageously comprises a conventional bandpass filter 72 connected to the output of mixer 70 for removing spurious signals and minimizing aliasing errors that would be introduced by digitizing; and a conventional digital Fourier analyzer 74 which digitizes the output of filter 72, Fourier transforms the digitized output, and selects the direct path propagation spectral line. Bandpass filter 72 preferably is configured to have a lower cutoff frequency of 500 Hz and an upper cutoff frequency of 2000 Hz. A Microlab DA-2FN divider, two Avantek AMM4033N amplifiers, a Watkins-Johnson WJM1G mixer, a Krohn-Hite 3343R filter, and a Hewlett-Packard HP5451A Fourier Analyzer advantageously comprise divider 60, amplifiers 65 and 67, mixer 70, filter 72, and Fourier analyzer 74, respectively.

The operation of system 10 in the acquisition of the TDS data will now be described. The range of microwave frequencies employed in the sweep is determined by setting the voltage range of the ramp from single sweep generator 55. The frequency range is selected to avoid broadening of the TDS spectral line. Control computer 46 is so programmed that a square array of a predetermined number of sample locations, corresponding to image pixels, are scanned by scanner 20. Computer 46 is further programmed such that, based on inputs from the system operator as to the incremental values of the sample locations in the X and Y coordinate directions the approximate number of stepping motor pulses needed to drive antennas 24 and 25 to each sample location is determined, using conventional calculations. Computer 46 then generates, for each individual pixel measurement, control signals using the outputs of transducers 36, as converted by converter 42, and well-known conventional servo-control feedback techniques to actuate motors 34 so as to drive antennas 24 and 25 to within preferably 0.01 mm of the desired location. (It will be appreciated by those of ordinary skill in the art that positioning of antennas 24 and 25 using conventional servo control techniques entails comparing the actual position of the antennas, as sensed by transducers 36, with the desired position, as determined by computer 46, and producing control signals for motors 34 in dependence on the comparison which cause the antennas to be displaced to within a predetermined distance from the desired position.)

Function generator 56 preferably is operated in an automatic mode such that oscillator 54 repetitively produces a swept frequency output signal at a predetermined rate. The rate at which oscillator 54 is actuated to generate output signals is determined by the sampling time of the electromechanical scanner 20. With the specific embodiment of analyzer 74 noted hereinabove, a repetition rate of one output signal per second has proved satisfactory.

Once antennas 24 and 25 are positioned for a sample location, computer 46 generates control signals to actuate Fourier analyzer 74, which is configured to digitize the output of filter 72 and to produce a Time Delay Spectrum from which the amplitude of the spectral line corresponding to the direct ray path of propagation through the target is determined. Based on the Time Delay Spectroscopy techniques disclosed in applicants' aforementioned U.S. Pat. No. 4,135,131, analyzer 74 advantageously is configured either to detect the spectral line having the largest amplitude and produce an output corresponding to the amplitude thereof, or to produce an output corresponding to the amplitude of the spectral line having a predetermined reference spectral frequency. As a first approximation, the reference spectral frequency is chosen by producing another time delay spectrum with TDS system 50, but with the target removed from interrogation system 21, and determining the spectral frequency of the highest amplitude spectral line of this spectrum, which corresponds to the direct propagation path between the antennas.

Analyzer 74 advantageously also is configured so as to be capable of detecting the spectral lines having a spectral frequency which falls within a predetermined range of propagation delays in the vicinity of the propagation delay corresponding to the above-mentioned reference spectral frequency, and to produce a plurality of outputs corresponding to the amplitude of the respective spectral lines within the range of frequencies. A plurality of images is then produced, each image being based on a set of "TDS data", described in more detail hereinbelow, which is obtained from the set of outputs for a corresponding one of the frequencies within the range of frequencies. The plurality of images thus produced are then compared. The images obtained from the TDS data collectively contain the direct path of propagation through the target.

Computer 46 preferably is programmed so as to repeat this cycle such that target 300 is scanned in a raster pattern without flyback at the end of each line, and such that the output of analyzer 74 for each sample location is stored in memory 44. The values of the set of outputs stored in memory 44 will for the sake of clarity be referred to hereinafter as the "TDS data".

Sampling increments of approximately 1.5 mm or less in both azimuth and elevation have been found to provide satisfactory resolution.

As will be appreciated by those of ordinary skill in the art, an analog embodiment of spectrum analyzer 73 may also be employed, to minimize the time for data acquisition.

The number of sample locations, or image pixels in the scanned array represents a compromise between the resolution desired and the length of time which can be tolerated for the data acquisition process. As an example, a 64×64 array, which provides satisfactory resolution, required four hours to collect the data using the scanning and measurement apparatus described hereinabove. As noted above, it is also possible with conventional special purpose equipment to reduce the scan time substantially. For example, the TDS calculations could be performed by analog processing which detects the spectral peak that corresponds to the direct ray path of propagation to reduce scan time.

Referring to FIG. 1, once the TDS data have been acquired, the set of data for the reference spectral frequency or for each spectral frequency within the predetermined range of propagation delays which has been measured is processed in the manner to be described hereinbelow using a suitably programmed conventional digital computer 60 to generate corresponding control signals which are applied to the input of a conventional display 70 to produce a corresponding facsimile image of the target. Video images are readily produced with an embodiment of display 70 comprising a Conrac 525 line video monitor and associated Comptal terminal.

For each set of TDS data from which an image is to be generated, the first step in the processing sequence is to convert the data to digital form, if not already in that form, using conventional conversion techniques. The next step is to transform the digital data from time domain to frequency domain using conventional Fourier transform techniques.

The transformed data is then processed as set forth in applicant's aforementioned Physiologic Facsimile Imaging application. Thus, the data is stored into column order. The sorting advantageously is done using conventional two dimensional array FORTRAN element successor rules.

The next step is to truncate, if necessary, the sorted TDS data in bit length in order that control signals can be readily generated which are compatible with the particular embodiment of display 70 being used. Using the preferred apparatus specified hereinabove, the data generated by Fourier analyzer 74 must be truncated from its original 16 bit length to the seven most significant bits.

In order to enhance and preserve the resolution of the facsimile image which is obtained, the sorted or truncated data is digitally magnified. This advantageously is accomplished by interpolation of the data with a cubic spline, as is known in the art. Magnification of a $64 \times 64 \times 7$ bit data set to a $256 \times 256 \times 7$ bit set has been found to produce satisfactory results using the specific embodiment of display 70 for video imaging noted hereinabove.

Figure 2:
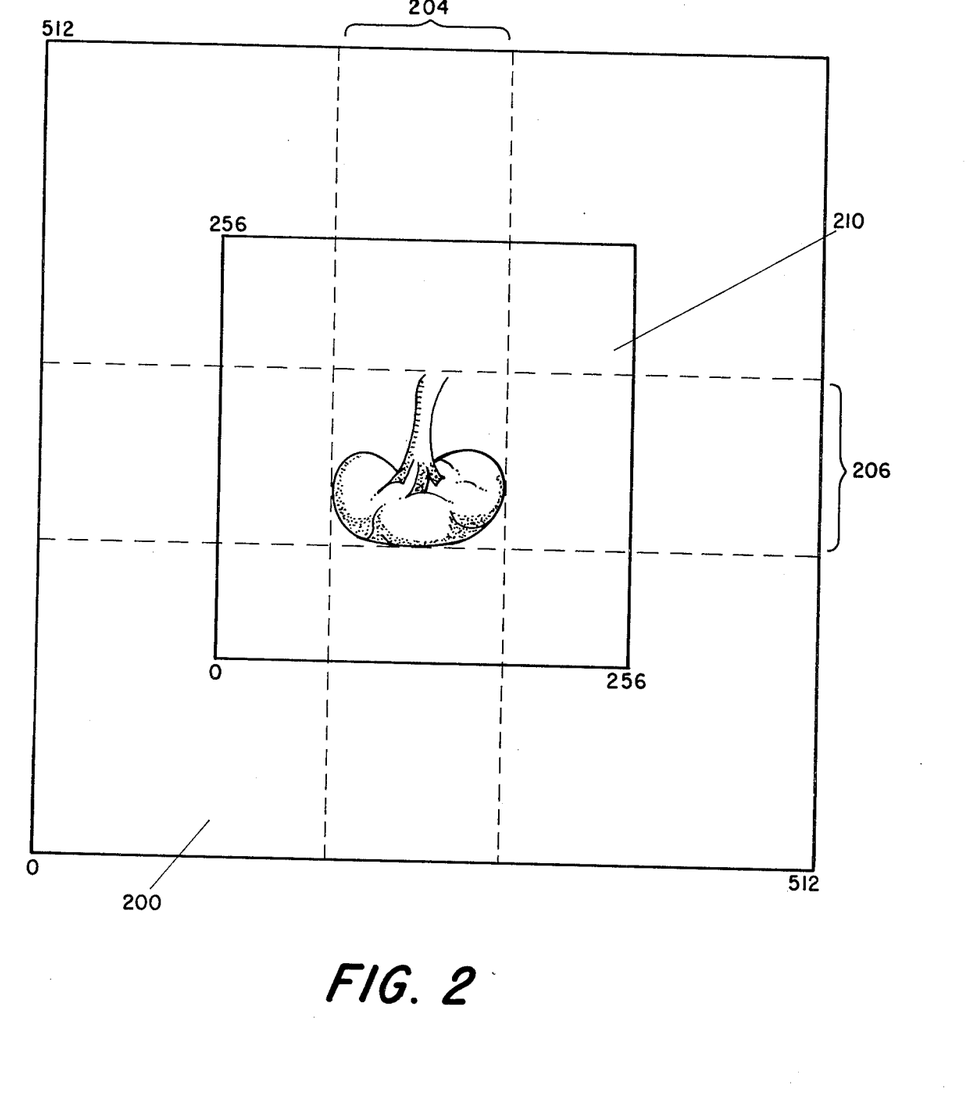
FIG. 2 is a diagrammatic illustration of a subimage which is advantageously generated to determine the desired mapping function to be used in accordance with the present invention.

In order to make better use of the dynamic range of display 70 and thus to allow the contrast between target portions and background portions of the facsimile image to be enhanced, the next step is to grey scale or variate map the magnified data into further data in accordance with a predetermined mapping function so as to distribute the actual values of the TDS data corresponding to the target or selected anatomical features thereof (which typically are contained within a small range of original pixel values) over the entire dynamic range of pixel values for the image display being employed. The mapping thus operates to select the range of data values which represents the target and to exclude background or other irrelevant data. Advantageously, the mapping function is empirically determined by a histogram analysis of the distribution of the magnified TDS data, and selection of a mapping function which enhances the contrast, and hence the delineation, between selected anatomical "landmark" features of the target and/or between selected landmark features and selected features of the background as is shown in FIG. 2. Advantageously, computer implementation of the histogram analysis is facilitated by precisely positioning the target without scanner 20 such that the TDS data corresponding to the physical location of the target and of the desired anatomical features thereof can be correlated, using well-known, conventional techniques, with the matrix coordinates identifying the location of the corresponding sample location, as shown in FIG. 2, within the scanning array, and hence of the data, within memory 44. More specifically, the histogram analysis advantageously entails generating, in accordance with conventional imaging techniques, an image on display 70 using the magnified TDS data such that the TDS data image is centered within a zero padded image plane which is coextensive in size with the image raster of display 70. Referring to FIG. 2, which diagrammatically depicts such an image, portion 200 constitutes the zero padded portion of the image, and portion 210 constitutes the TDS data portion (including background). (It will be appreciated by those of ordinary skill in the art that the content of portion 210 has been figuratively depicted by a pictorial sketch of a kidney, and that the actual display is more nearly similar to the image depicted in FIG. 9, but without the detail.)

The relevant subimage data, for example, that corresponds to the entire target 300 which is to be mapped, is then identified based on the pixel locations of the subimage data within the generated image. Referring to FIG. 2, the portion defined by the intersection of portions 204 and 206 of the image constitutes the subimage portion of the TDS data portion corresponding to the target being scanned.

Figure 3:
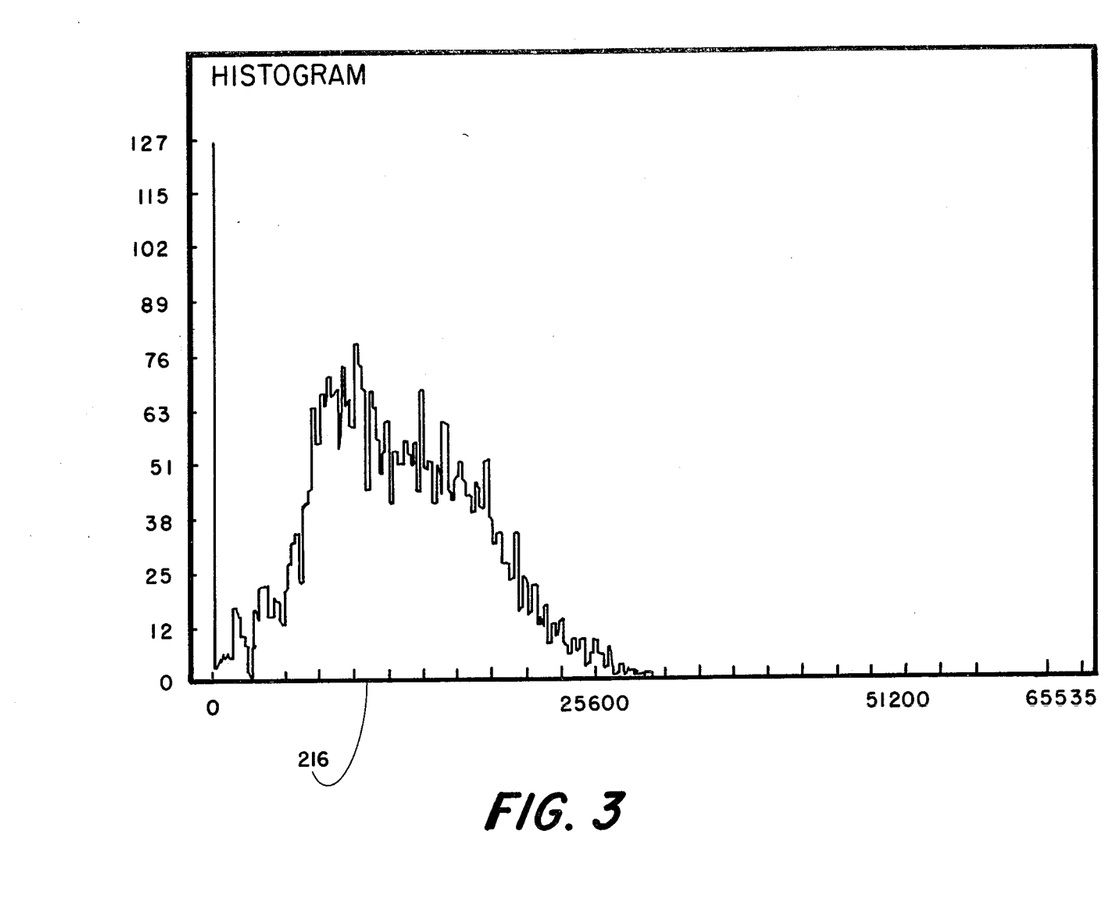
FIG. 3 is a graphical representation of a first histogram for the TDS data from which images of the type illustrated in FIG. 8 were obtained in accordance with the present invention.
Figure 4:
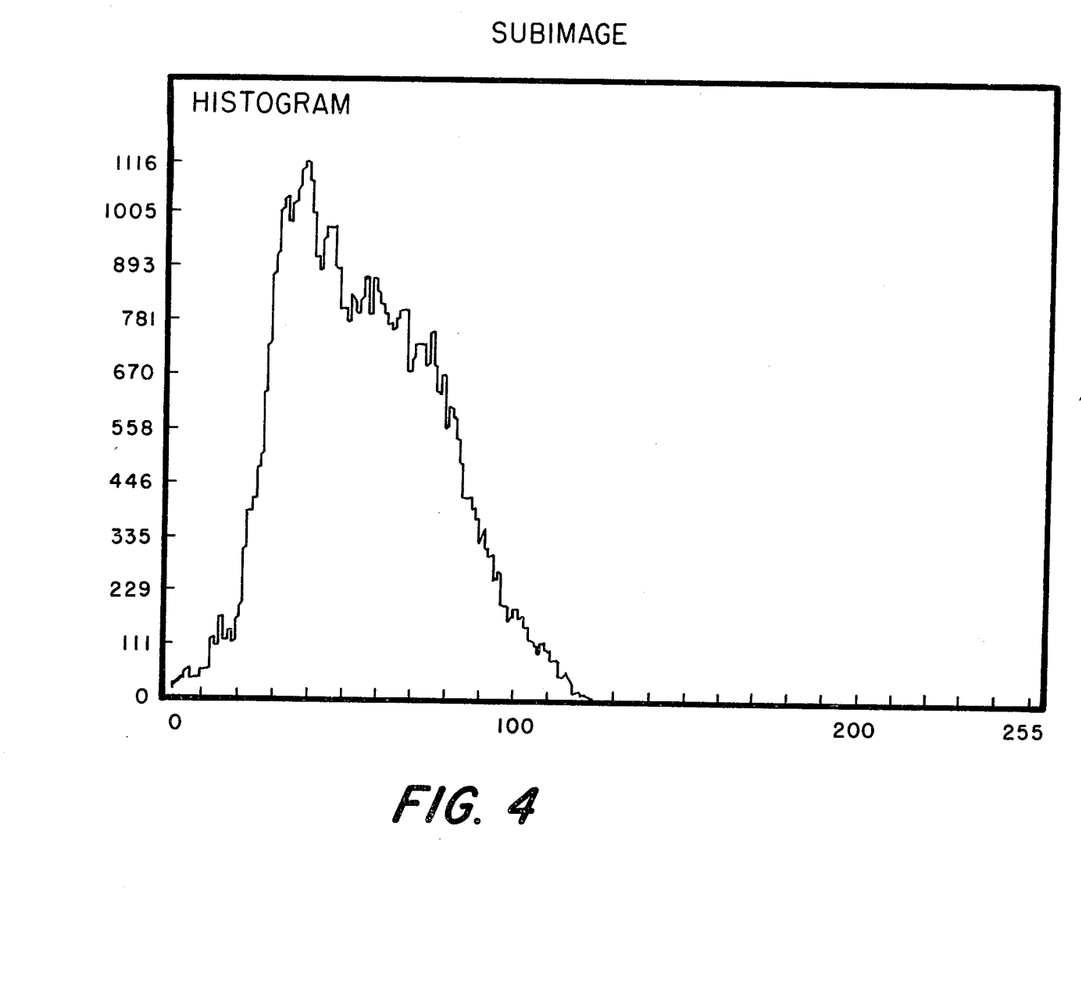
FIG. 4 is a graphical representation of a second histogram used in determining the desired mapping function to be used in accordance with the present invention.

The subimage pixels are then correlated to the TDS data and an expanded histogram of the selected TDS data is generated, which is then analyzed using conventional empirical techniques to determine an appropriate mapping function for the selected TDS data. As an illustrative example, the complete histogram for all of the TDS data collected for an image is shown in FIG. 3, and the expanded histogram of the selected TDS data is shown in FIG. 4. Arrow 216 in FIG. 3 denotes the general location in the complete histogram of the selected TDS data displayed in the expanded histogram of FIG. 4.

The effect of the subimage determination is to alter the histogram of pixel value distribution from the total scan to that of just the target. The TDS data from which the facsimile image is to be generated thus covers a range of only approximately 120 intensity values instead of a range of approximately 32,767 values. Further, the distribution of subimage pixel values tends to more nearly approximate a unimodal distribution, which is more suitable to contrast enhancement.

Figure 5:
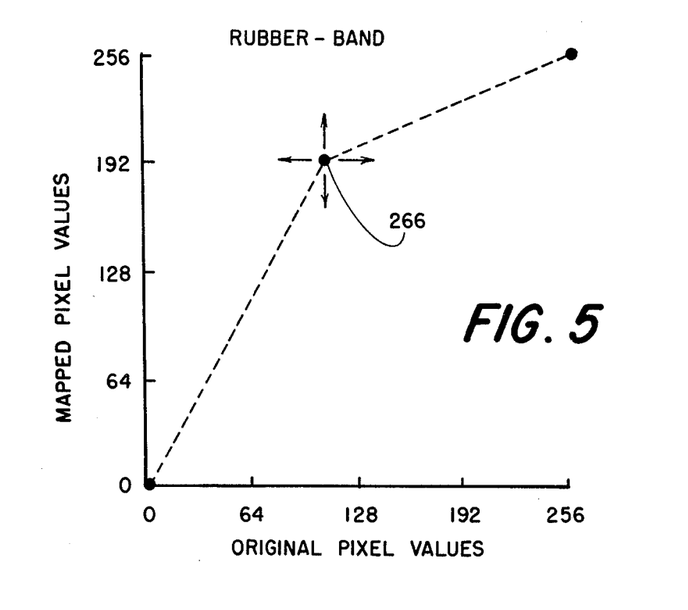
FIGS. 5 and 6 are graphical representations of preferred mapping functions that have been determined in accordance with the present invention.
Figure 6:
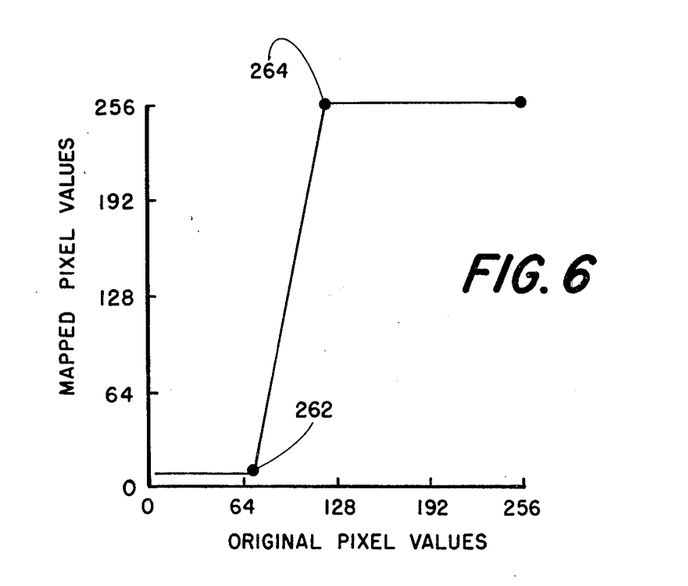

Both a ramped linear, and a two-piece hinged mapping function have proven advantageous. Preferred embodiments of ramped and hinged functions which have provided acceptable image of a canine kidney, based on the histogram illustrated in FIG. 4, are illustrated in FIGS. 5 and 6, respectively. As will be appreciated by those of ordinary skill in the art, the ramp function linearly "stretches" a continuous subset of values to cover the entire dynamic range of pixel values for the display. Referring to FIG. 6, any TDS data values equal to or less than the left hand margin or threshold 262 are mapped into the "0" (black or "fulloff") display pixel value, and any data values equal to or greater than the right hand margin or theshold 264 are mapped into the "255" (white or "full-on") display pixel value. The hinged mapping functon (known as a "rubber band" function) is characterized by a piecewise linear function with fixed points at the maximum and minimum pixel values of the display, and a selectively positionable point, denoted 266 in FIG. 5, therebetween which serves as a hinge. The hinged mapping function achieves less stretching, or contrast enhancement, than the ramped function, but it does have the advantages of preserving more of the original range than does the ramp function, and of not forcing any original data values into new values corresponding to either minimum or maximum display pixel values, which avoids the blocking effect of the ramp function.

Figure 7:
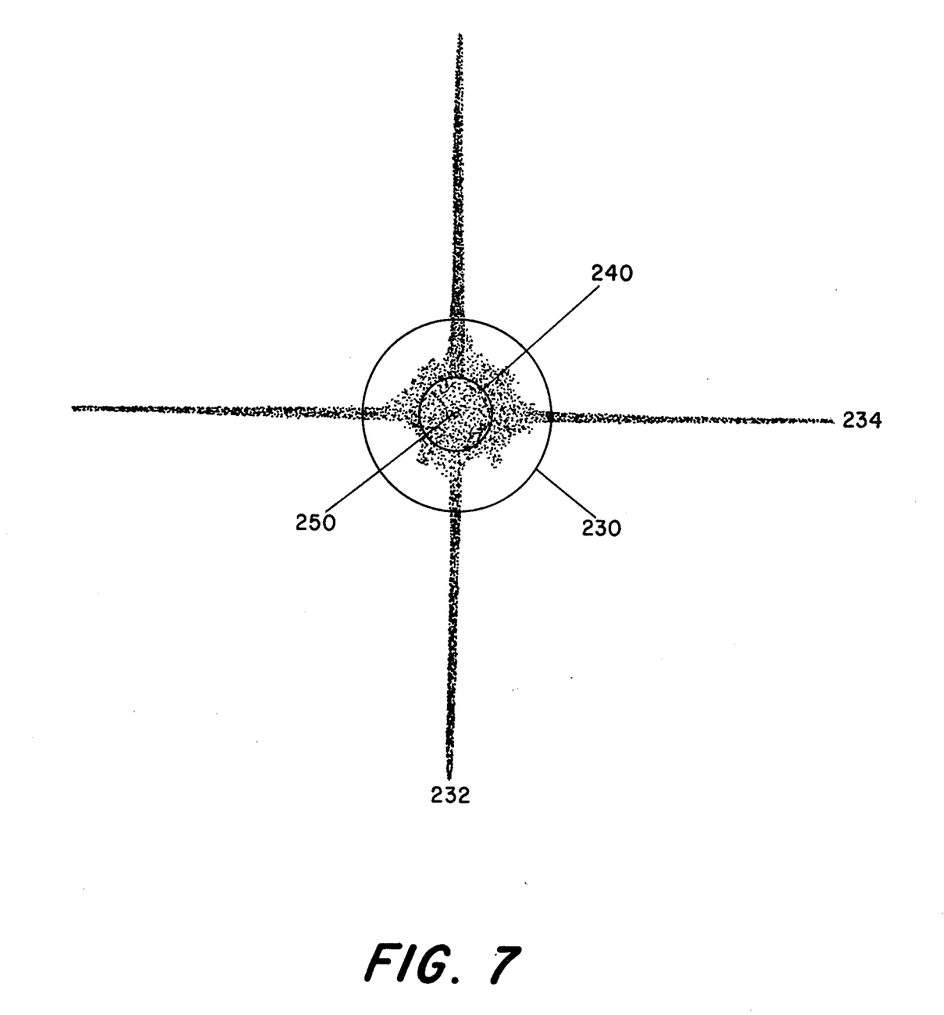
FIG. 7 is a diagrammatic representation of the power spectral density function and control signal definitions applied to the TDS data from which the image illustrated in FIG. 8 was obtained.

The next step is to obtain control signals for display 70 by filtering the magnified and mapped data using a two dimensional band pass function (BPF) having predetermined control variates $R_1$ and $R_2$ (which are shown in FIG. 7 as 240 and 230, respectively) defining the lower and upper frequency limits, respectively thereof, such that the effect of low frequencies that correspond to global variations in the thickness of the target, and the effect of spurious high spatial frequencies resulting from the magnification of the data, are minimized. The BPF preferably is such as to provide a relatively smooth transfer function. A second order Butterworth transfer function has been found advantageous as the BPF, and is preferred over higher order function because of ringing problems associated with the latter type of function. The BPF advantageously is interactively implemented during computer processing by a process described in Wintz, P., and Gonzales, J., *Digital Image Processing*, Addison-Wesley, Reading (1978), wherein the operation is performed in the frequency domain. In accordance with the Wintz et al. process, the data to be filtered is two dimensional Fourier transformed, and the Fourier transform of the data is then multiplied by the BPF. As will be appreciated by those of ordinary skill in the art, when this process is implemented digitally, the two-dimensional sampled data version of the transfer function is used. The product of this multiplication is then inverse Fourier transformed to produce the display control signals. It is to be noted that the equivalent process of convolving the TDS data with the Fourier transform of the sampled data version of the transfer function may also be employed. Preferably, only even series of the BPF are employed, since they may be represented by cosine terms only, and are therefore free of phase shift. In addition, radially symmetric filter functions advantageously are used when the sampling increments in azimuth and elevation are equal. It will be appreciated by those of ordinary skill in the art that the BPF serves to reject all spatial frequencies below the value of control variate $R_1$ and to reject all spatial frequencies above the value of control variate $R_2$.

A preferred method of empirically determining advantageous values of control variates $R_1$ and $R_2$ comprises the steps of: (1) computing the two dimensional power spectral density (psd) function (which preferably is normalized for unity effective bandwidth) for the magnified and mapped TDS data; (2) selecting as the value of control variate $R_1$ the spatial frequency below which approximately 20% of the power is obtained, as determined from the psd function; and (3) selecting as a value of control variate $R_2$ the spatial frequency above which the high spatial frequencies representing noise introduced by the cubic spline operation of the magnification step are located.

It has been determined that advantageous values of control vairates $R_1$ and $R_2$ are obtained using a second order Butterworth BPF by placing the $-1$ dB points of the upper frequency limit of the BPF at $\pm f_{max}$, the folding frequency, where $f_{max} = 1/2\Delta X$, and $\Delta X$ is the spatial sampling increment used for collection of the image data; and by selecting, as variate $R_1$, the spatial frequency corresponding to the $-3$ dB point of lower frequency limit, and by selecting, as variate $R_2$, the spatial frequency corresponding to the $-1$ dB point of the upper frequency limit. In particular, a low normalized spatial frequency cutoff ($-3$ dB) of 20 cycles per unit length and a high normalized spatial frequency cutoff ($-3$ dB) of 75 cycles per unit length have been found to be advantageous values of control variates $R_1$ and $R_2$, respectively, based on a sampling increment of approximately 1.4 mm, and a display having a $512 \times 512$ raster and thus a corresponding maximum normalized frequency of 256 cycles per unit length.

The psd function may advantageously be obtained from the magnified and mapped TDS data by a cube root data compression of the data, followed by a line-by-line univariate fast Fourier transform (FFT) of the compressed data, followed by a matrix transposition (column for row substitution) of the resulting set of Fourier coefficients, followed by another series of FFT operations on a line-by-line basis of the transposed set of Fourier coefficients. The result is a bivariate FFT, which is then multiplied by the complex conjugate thereof to derive the psd function.

The psd function is preferably normalized for unity effective bandwidth, as noted hereinabove, in order to aid comparability between pictures.

As an aid to understanding, the bivariate Fourier transform referred to above is defined in an analytical, continuous notation as follows:

$$F\{S\} = \int_{-\infty}^{\infty} \int_{-\infty}^{\infty} s(x,y)\exp[-j2\pi(f_y y + f_x x)]dy\,dx$$

In general, the expression allows $s(x,y)$ to be a complex variable where the functional notation indicates x as the direction in azimuth and y as the direction in elevation. The complex exponential argument involves these two coordinates in the variates x and y as well as in the variates $f_x$ and $f_y$, which indicate frequency in x or azimuth and frequency in y or elevation. The script "F" Fourier transform of the variate in upper case letters on the right side of the equation. Since the term "frequency" is so often considered in the context of time, the description "spatial frequency" has been coined to denote this variate. The definition of spatial frequency is still similar to the general definition of frequency, in that is is the inverse of a "period", but now the period of the "wave" is defined in distance rather than in time. Thus, spatial frequencies are described in cycles per unit length. Since the sample data transform is based on discrete data rather than on continuous analytical functions, the computational procedure set forth hereinabove solves the following univariate sampled data equation for the set of Fourier coefficients representing orthogonal expansion of the magnitude and/or phase data which is being processed:

$$f_n = \tfrac{1}{2}a_o + \sum_{p=1}^{N} [a_p\cos 2\pi np/(2N+1) + b_p\sin 2\pi np/(2N+1)]$$

The well known solutions for the Fourier coefficients are $$a_p = \frac{2}{2N+1} \sum_{n=1}^{2N} f_n \cos 2\pi np/(2N+1)$$

and $$b_p = \frac{2}{2N+1} \sum_{n=1}^{2N} f_n \sin 2\pi np/(2N+1)$$

The variate f is once again a spatial frequency.

As a further aid to understanding, a diagrammatic representation as illustrated in FIG. 7 of a video image of the psd function for the magnitude component of the TDS data used to generate the facsimile image of a canine kidney which is described in more detail hereinbelow. The actual format of the display is that which would be produced by optical Fourier processing. However, since the data is a real valued dimensional spatial series, the description to follow is acceptable. The horizontal axis 234 is $f_x$ in the 2D transform. The vertical axis 232 is $f_y$ in the 2D transform. The spatial frequencies are displayed as positive and negative cycles per unit length proceeding from the origin, or center, of the axes. Thus, positive spatial frequencies in elevation are on the upper vertical coordinate, whereas negative frequencies are on the lower vertical coordinate. Similarly, positive spatial frequencies in azimuth are on the right hand horizontal coordinate, whereas negative frequencies in azimuth are on the left hand horizontal coordinate. The power spectral values are displayed in a video image of the psd function as dots of intensity proportional to the power spectral magnitude. The dots are located in the bivariate coordinate plane according to their respective Cartesian coordinate values for $f_y$ and $f_x$ (i.e., spatial frequency in elevation and azimuth). Maximum normalized spatial frequency on either axis is plus and minus (upper and lower, or right and left, respectively) 256 cycles per unit length, based on a 512×512 sample raster. Control variate $R_1$ is denoted by circle 240, and control variate $R_2$ is denoted by circle 230. The display origin is located at 250.

Before a hard copy of the facsimile image produced by display 70 is obtained, further control signals are produced by a filtering step wherein the facsimile image is either contrast stretched or high pass filtered with a simple 3×3 kernal to sharpen the slow rate of roll-off at the high frequency edge of the BPF. As is conventional, a monochromatic image may be overlaid with interactively generated contours to enhance the visibility of grey-scale differences. Pseudocolor images may also be generated by modifying the control signals using empirically determined color mapping algorithms, such as the "hot earth" red/orange/brown map, the "linear A" blue/green/violet, and the Ray C maps developed for the NASA Landsat Program. The number of hues preferably is minimized in order to reduce the perceptual distraction that can accompany a pseudocolor display.

It is to be noted that the truncating, magnifying, histogram production, mapping, psd function computing, filtering, contouring and pseudocoloring steps described hereinabove advantageously are interactively implemented by adapting the corresponding adaptable general purpose subroutines of the Digital Image Analysis Laboratory (DIAL) computer implemented image generating system developed by the United States Army Topographical Laboratories. The DIAL system is described in Schrook, B. L., *DIAL Programmers Guide*, U.S. Army Topographical Laboratories, Ft. Belvoir (1978). As will be appreciated by those of ordinary skill in the art, implementation of the filtering step using the DIAL system entails placing the mapped TDS data at the center of a zero padded 512×512×8 bits image plane.

Figure 8:
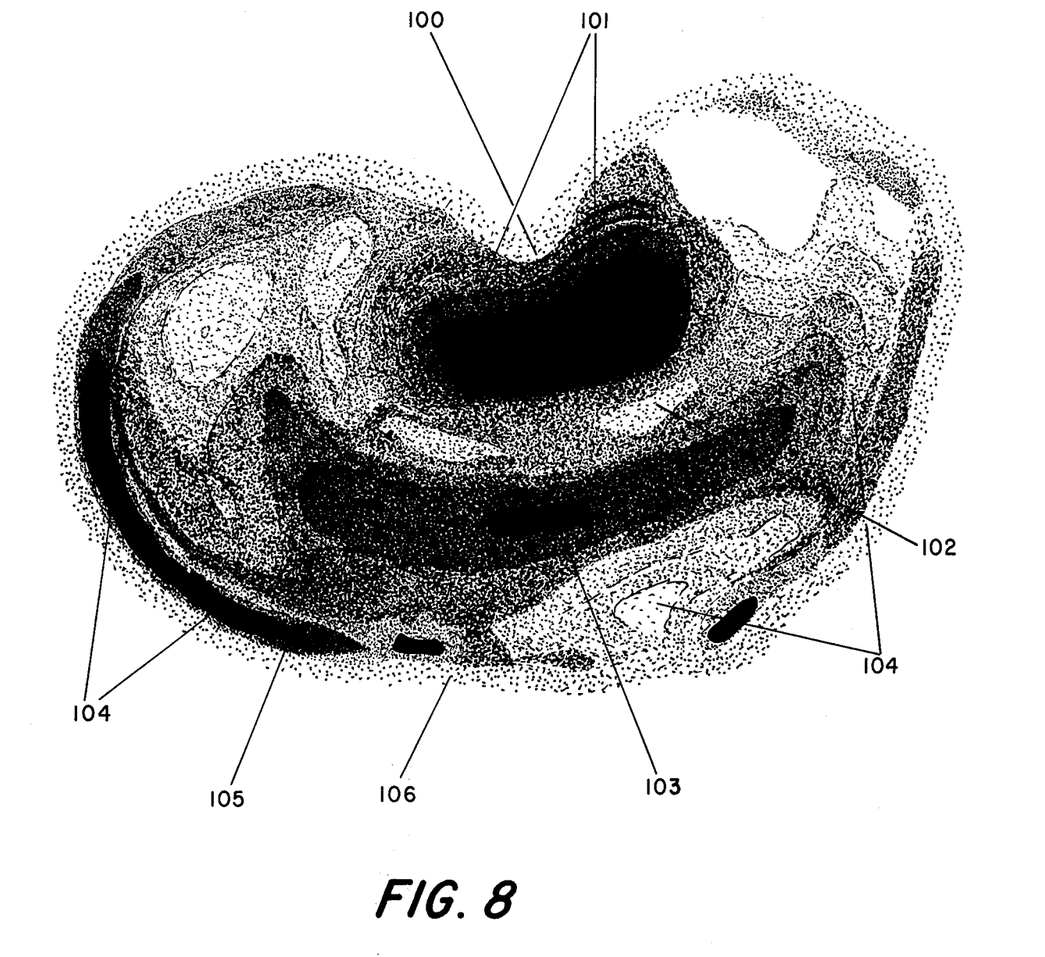
FIG. 8 is a diagrammatic representation of the facsimile image shown in the photograph attached hereto as Exhibit A, which image was obtained in accordance with the present invention.

FIG. 8 diagrammatically depicts a monochrome video image which has been obtained in accordance with the present invention from TDS data obtained for a fresh isolated canine kidney. The dielectric medium constituting body 23 was water. The kidney had been removed from a mixed breed dog immediately before the scan. The ureter was temporarily cannulated to fill the pelvis with physiologic saline. The cannula was removed concurrently with ligation of the ureter prior to attaching this and the hilar vessels to the mounting arm by purse string sutures. The capsule was carefully preserved intact except for a 4-0 purse string suture in the dependent margin to support ca. 10 grams of weight to counteract the buoyancy of the organ.

In general, the TDS facsimile image which is produced is a two dimensional map of the power spectral ordinate at a specific Time Delay Spectroscopy frequency which is related to propagation delay. Thus, the facsimile image represents a partitioning of the total energy received by antenna 25 according to propagation delay. Thus the dark or "black" portions of the image cannot be associated with high general loss, but only with comparatively less energy reaching the receiving antenna within a specific range of differential propagation delays. However, the black brightness level of the display does represent minimum received energy at the chosen Time Delay Spectroscopic frequency, and the white brightness level of the display does represent the maximum received energy, and as between different regions of the target, the brightness of the display is indicative of the relative insertion loss produced by the target.

It is also to be noted that the unprocessed range of the Time Delay Spectroscopy spectral ordinates actually selected covered approximately three orders of magnitude. As a result, unimodal distributions were less commonly encountered and, therefore, any single mapping can represent only a smaller fraction of the total range. Further, limitations of the embodiments of the apparatus which were employed, such as the maximum rate at which sweep oscillator 54 could be swept, the maximum speed of analog-to-digital conversion in analyzer 74, and the maximum number of points that could be digitized in a sweep, contributed to limit the differential delay resolution of the image depicted in FIG. 8.

Referring to FIG. 8, which approximates the actual image as shown in the photograph attached hereto as exhibit A, the cardinal features of a facsimile image produced from the TDS data are as follows: portion 100 corresponds to the renal hilus, portion 101 corresponds to the renal pelvis, portion 102 corresponds to the medullary inner stripe, portion 103 corresponds to the medullary outer stripe, portion 104 corresponds to the cortical lobulations, portion 105 corresponds to the cortex corticis, and portion 106 corresponds to the renal capsule.

It will be appreciated by those of ordinary skill in the art that the ability to identify anatomical landmarks in these images demonstrates the utility of microwave imaging for physiologic imaging, since these anatomical landmarks may be usefully related to known features of renal physiology. The hilus is known to be a region of ingress and egress of major blood vessels and the origins of the ureter. The pelvis is known to be a muscular cistern for collection of urine. The inner medullary stripe is known to contain the bases of the medullary pyramids which empty into the pelvis via the calyces. Microscopically, this is a region of high population of collecting tubules and the thin loops of Henle where the final steps of osmotic concentration take place. The medullary outer stripe is known to be a region of high population density for the thick loops of Henle and early collecting tubules. Major water and electrolyte transport takes place in this region. The cortical lobulations are known to be regions of high population density of glomeruli as well as proximal and distal convoluted tubules. The lobulations are known to be formed by the interlobular vascular bundle. These are regions of blood ultrafiltration and transport, respectively. The cortex corticis is known to be a region relatively devoid of glomeruli where the proximal and distal tubules of glomeruli located distal to the cortico-medullary are found. This is a region where reabsorption and secretion takes place. Lastly, the capsule is known to be a tough, fibrous envelope of connective tissue which forms the outer boundary of the organ.

Thus, the anatomical landmarks which can be identified in the images correspond to known regions of functional specialization within the kidney. As a result, the image represents functional/physiological specialization is an isolated organ without dielectric enhancement by agents analogous to the radiopaque dye used in x-ray intravenous pyelography. It is to be noted that a distinguishing characteristic of microwave imaging in accordance with the present invention is that x-ray pyelography provides primarily structural information concerning the pelvis and calcyes, with the functional information that can be derived therefrom being limited to the rate of dye clearance. Moreover, the facsimile images which can be obtained in accordance with the present invention do not require enhancement by filling the pelvis/calcyes with non-physiologic materials as is the case with x-ray pyelography.

Although the invention has been described with respect to exemplary embodiments thereof, it will be understood that variations and modifications can be effected in the embodiments without departing from the scope or spirit of the invention.

We claim:

1. A microwave imaging method of producing a physiologic facsimile image of a biological target on an image display device in which multipath contamination is minimized, comprising the steps of:
   (a) for each one of a plurality of sample locations which are spaced so as to define a two-dimensional array, producing a time delay spectrum wherein the frequency of each spectral ordinate represents the instantaneous differential propagation delay between a first microwave signal which has been propagated through the target and a second microwave signal, initially corresponding to said first microwave signal, which has been propagated through means having a predetermined propagation delay, and measuring the amplitude of the spectral ordinate corresponding to the direct ray path of propagation through the target, so as to obtain a set of data;
   (b) processing said set of data to obtain a corresponding set of control signals for the display device; and
   (c) producing a two-dimensional image array on the display device using said set of control signals, and thereby obtaining the facsimile image.

2. The microwave imaging method of claim 1 wherein said first and second microwave signals are derived from a constant amplitude swept signal in which the frequency varies linearly from a first frequency to a second frequency in a predetermined time period.

3. The microwave imaging method of claim 2 wherein said first frequency is approximately 3143 MHz and said second frequency is approximately 3763 MHz and said predetermined time period is approximately 15 msec in duration.

4. The microwave imaging method of claim 2 wherein said time delay spectrum is produced by multiplying said first and second microwave signals in a mixer and said amplitude measuring comprises digitizing the output of a filter connected to the output of said mixer, and measuring the amplitude of the spectral line having the largest amplitude.

5. The microwave imaging method of claim 2 wherein said first microwave signal is propagated using a remote interrogation system comprising a liquid medium having a high relative dielectric constant and in which the target is immersed, and a pair of selectively positionable microwave antenna probes immersed in said liquid medium in spaced relationship to the target and such that the target is coupled thereto by said liquid medium; said time delay spectrum is produced by multiplying said first and second microwave signals in a mixer; and said amplitude measuring comprises digitizing the output of a filter connected to the output of said mixer, and measuring the amplitude of the spectral line having a frequency corresponding to a predetermined reference frequency determined by the highest amplitude of a time delay spectrum produced by mixing a further microwave signal, initially corresponding to said first microwave signal, and which has been transmitted between said antenna probes in the absence of the target, with said second microwave signal.

6. The microwave imaging method of claim 1 further comprising the step of contrast stretching or high pass filtering the facsimile image so as to facilitate photographic reproduction of the displayed image.

7. The microwave imaging method of claim 3 wherein the center-to-center distance between sample location in both azimuth and elevation is less than or equal to approximately 1.5 mm.

8. The microwave imaging method of claim 1 wherein the sample locations are scanned in a raster pattern sequence without flyback at the end of each line.

9. The microwave imaging method of claim 1 wherein said set of data is in digital form and said processing step comprises the steps of:
   (a) transforming said set of data from time domain to frequency domain;
   (b) sorting said transformed set of data into column order;

(c) magnifying data derived from said sorting step so as to enhance and preserve the resolution of the image;

(d) mapping data derived from said magnifying step into further data using a predetermined mapping function so as to enhance the contrast between selected portions of the image; and (e) obtaining said set of control signals by filtering data derived from said mapping step using a band pass function which rejects spatial frequencies below a predetermined first frequency and/or rejects spatial frequencies above a predetermined second frequency so as to minimize, respectively, the effects of variations in the thickness of the target and/or spurious frequencies resulting from said magnifying of step (c).

10. The microwave imaging method of claim 9 wherein said magnifying step (c) comprises the steps of interpolating data derived from said sorting step (b) with a cubic spline function.

11. The microwave imaging method of claim 9 wherein said mapping function of step (d) is determined by analyzing a histogram of data derived from said magnifying step (c) to select a mapping function which distributes data derived from said magnifying step and corresponding to the target or selected anatomical features thereof over the entire dynamic range of pixel values for the display device, and which excludes other data derived from said magnifying step.

12. The microwave imaging method of claim 9 wherein said mapping function is a ramp function.

13. The microwave imaging method of claim 9 wherein said mapping function is a two-piece hinged function.

14. The microwave imaging method of claim 9 wherein said predetermined first frequency is determined by computing the psd function of data derived from said mapping step and determining the spatial frequency below which approximately 20% of the power is contained in the data from which said psd function is computed.

15. The microwave imaging method of claim 9 wherein said predetermined second frequency is determined by the folding frequency as established by the sampling increment at the time of data collection.

16. The microwave imaging method of claim 14 or 15 wherein said psd function is normalized for unity effective bandwidth.

17. The microwave imaging method of claim 9 wherein said filtering comprises the steps of two-dimensional Fourier transforming data derived from said mapping step, multiplying data derived from said Fourier transforming by said band pass function, and inverse Fourier transforming data derived from said multiplying step.

18. The microwave imaging method of claim 9 wherein said band pass function is radially symmetric.

19. The microwave imaging method of claim 2 wherein said first microwave signal is propagated using a remote interrogation system comprising a liquid medium having a high relative dielectric constant and in which the target is immersed, and a pair of selectively positionable microwave antenna probes immersed in said liquid medium in spaced relationship to the target and such that the target is coupled thereto by said liquid medium; said time delay spectrum is produced by multiplying said first and second mircowave signals in a mixer; and said amplitude measuring comprises digitizing the output of a filter connected to the output of said mixer, and measuring the amplitude of the spectral line having a frequency corresponding to a predetermined reference frequency determined by measuring the amplitude of a time delay spectrum produced by mixing a further microwave signal, initially corresponding to said first microwave signal, and which has been transmitted between said antenna probes in the absence of the target, with said second microwave signal at each one of a plurality of frequencies within a predetermined range wherein the plurality of facsimile images so produced encompass the frequency at which the amplitude of the time delay spectrum is highest as well as adjacent frequencies among which the direct ray path is collectively represented.

\* \* \* \* \*